United States Patent [19]
Collin et al.

[11] Patent Number: 5,846,732
[45] Date of Patent: Dec. 8, 1998

[54] PEPTIDES OF CASEINOMACROPEPTIDE, ANTIBODIES AGAINST THE SAID PEPTIDES, AND USES

[75] Inventors: Jean-Claude Collin, Poligny; Jean-Louis Perrod, Bage-Le-Chatel, both of France

[73] Assignee: Sanofi Diagnostics Pasteur, La Coquette, France

[21] Appl. No.: 256,018

[22] PCT Filed: Jan. 8, 1993

[86] PCT No.: PCT/FR93/00014

§ 371 Date: Aug. 10, 1994

§ 102(e) Date: Aug. 10, 1994

[87] PCT Pub. No.: WO93/14117

PCT Pub. Date: Jul. 22, 1993

[30] Foreign Application Priority Data

Jan. 10, 1992 [FR] France ................................. 92 00188

[51] Int. Cl.$^6$ ........................... G01N 33/53; A61K 38/08; C12N 5/12; C07K 16/18
[52] U.S. Cl. ...................... 435/7.1; 435/7.92; 435/70.21; 435/346; 424/139.1; 424/141.1; 424/172.1; 530/327; 530/328; 530/329; 530/330; 530/387.1; 530/387.9; 530/388.1
[58] Field of Search .............................. 530/387.1, 387.9, 530/388.1, 388.9, 330, 329, 328, 327, 326, 325, 350; 435/70.21, 7.92, 7.1; 424/184.1, 185.1, 130.1, 139.1, 141.1, 172.1

[56] References Cited

PUBLICATIONS

Seaver, S. Genetic Engineering News vol. 14, pp. 10, 21, Aug. 1994.
Raha, S. et al. Blood 72(1): 172–178, Jul. 1988.
Otani, H. M. et al. Milchwissenschaft 46 (11) 689–693, 1990.
Otani, H. M. et al. Milchwissenschaft 46 (1): 23–26, 1991.
Koher, G. et al. Nature 256: 495–497, Aug. 1975.
Sevier, E. D. et al. Clinical Chem. 27: 1797–1806, Nov. 1981.
Feng et al. [Hybridoma 8(2):223–230 (1989)].
Kang et al. J. Dairy Sci. 71(1):29–40 (1988).
Mäkelä et al. [*Immunochemistry*, (1986), Blackwell Scientific Publications, CA, chapter 3, Haptens and carriers, pp. 3.1–3.13].
Leonil, J. et al. The Biochemical Journal 271(1):247–252 (1990).
Drohse, H.B. et al. Biochemica et Biophysica Acta 995(3):221–224 (1989).
Mehrens, H.A. et al. Chemcial Abstracts 105:560 (Abst #113714r) (1986).
Otani, N. et al. Biological Abstracts 91(7):AB–390 Abst #71946 (1991).

*Primary Examiner*—Frank C. Eisenschenk
*Assistant Examiner*—Evelyn Rabin

[57] ABSTRACT

The present invention presents an antigenic peptide whose amino acid sequence comprises a fragment of the caseinomacropeptide (CMP) sequence, which peptide is characterized in that it carries at least one epitope of CMP. These peptides exhibit no or little cross-reactivity with K-casein. When these peptides are used as immunogens, they make it possible to obtain specific anti-CMP antibodies. Also disclosed is a process for detecting the presence of cow's milk CMP in milk and milk products, using the above antibodies. Further presented are diagnostic reagents for the assay of CMP, which reagents are characterized in that they comprise at least one peptide, antigenic composition, or anti-CMP antibody of the present invention.

18 Claims, 3 Drawing Sheets

```
124                 133                                          141                              149
Thr-Ile-Ala-Ser-Gly-Gln-Pro-Thr-Ser-Thr-Pro-Thr-Thr-Gln-Ala-Val-Gln-Ser-Thr-Val-Ala-Thr-Leu-Gln-Asp-Ser
                 PEPTIDE 2                                                  PEPTIDE 3
                 (SEQ. ID NO. 4)
```

```
148                  157                                   164                        169
Asp-Ser-Pro-Glu-Val-Ile-Glu-Ser-Pro-Pro-Gln-Ile-Asn-Thr-Val-Gln-Val-Thr-Ser-Thr-Ala-Val-OH
                 PEPTIDE 5                             PEPTIDE 6
                 (SEQ. ID NO. 5)                      (SEQ. ID NO. 2)
```

PEPTIDE 4

FIG. 2

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:1:

Met   Ala   Ile   Pro   Pro
    1                               5

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:2:

Ser   Pro   Pro   Glu   Ile   Asn   Thr   Val   Gln   Val
    1                       5                                10

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( D ) TOPOLOGY: linear     ( i i ) MOLECULE TYPE: peptide ( x i ) SEQUENCE DESCRIPTION: SEQ ID NO:3:

Lys Thr Glu Ile Pro Thr Ile Asn Thr Ile
1               5                   10

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:4:

Thr Ile Ala Ser Gly Glu Pro Thr Ser Thr
1               5                   10

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:5:

Asp Ser Pro Glu Val Ile Glu Ser Pro Pro
1               5                   10

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:6:

Met Ala Ile Pro Pro Lys Lys Asn Gln Asp Lys
1               5                   10

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:7:

Met Ala Ile Pro Pro Lys
1               5

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:8:

Met Ala Ile Pro Pro Lys Lys
1               5

( 2 ) INFORMATION FOR SEQ ID NO:9:

( i ) SEQUENCE CHARACTERISTICS:
      ( A ) LENGTH: 8 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:9:

Met  Ala  Ile  Pro  Pro  Lys  Lys  Asn
   1                   5

( 2 ) INFORMATION FOR SEQ ID NO:10:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:10:

Met  Ala  Ile  Pro  Pro  Lys  Lys  Asn  Gln
   1                   5

( 2 ) INFORMATION FOR SEQ ID NO:11:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:11:

Met  Ala  Ile  Pro  Pro  Lys  Lys  Asn  Gln  Asp
   1                   5                    1 0

PEPTIDES OF CASEINOMACROPEPTIDE, ANTIBODIES AGAINST THE SAID PEPTIDES, AND USES

The invention relates to a process which makes it possible to evaluate the degree of proteolytic denaturation of milk and milk products.

Proteolysis phenomena and, in particular, those due to bacterial proteases are responsible for a reduction in the quality of milk products.

The bacteria responsible for these phenomena are essentially Gram-negative bacteria, and especially Pseudomonas. These are psychrotrophic bacteria which are capable of developing at low temperature; the storage of milk at 4° C. favours the development of these bacteria at the expense of other species.

The action of proteases from psychrotrophic bacteria has been studied essentially with respect to casein. It seems that the fraction which is most rapidly degraded is K-casein; β-casein is also substantially attacked, and, to a lesser degree, αs1-casein is also degraded. Proteolysis of K-casein by psychrotrophic bacteria proteases releases a peptide of about sixty amino acids (for example 64 amino acids for cow's milk), caseinomacropeptide (CMP), also called glycomacropeptide (GMP), and corresponding to the C-terminal end of K-casein.

The protease activity of psychrotrophic bacteria is thermoresistant and is stable to UHT sterilisation treatments. The persistence of this activity in UHT products reduces the shelf life of these products and their organoleptic qualities. It is therefore desirable to have a test which makes it possible to evaluate the proteolysis (or the proteolytic potential) due to psychrotrophic bacteria in milk and milk products.

Such a test, when performed on milk on arrival at the dairy factory, will make it possible to determine the treatments and processing operations which are most suitable for the quality of the milk received. It would thus be possible to avoid certain manufacturing faults (jellification of UHT milks, bitter flavours, rancidity, decrease in cheese yields).

Furthermore, such a test would also be very useful for cheese manufacturing. Indeed, proteolytic enzymes from psychrotrophic bacteria definitely play a role in the maturing of cheese. Determination of the potential proteolytic activity before manufacturing would make it possible to better control the maturing by varying the ripening conditions.

Several techniques have consequently been proposed with the aim of evaluating proteolytic activity in milk, and in particular that due to psychrotrophic bacteria.

It has for example been proposed to directly evaluate the psychrotrophic flora responsible for proteolysis. This method, which involves techniques for culturing and enumerating bacteria, has all the disadvantages relating thereto; it is necessary to have a relatively large amount of specific equipment and a specialised staff and, on the other hand, the results are obtained only after the period required for the growth of the bacterial cultures. Recently, rapid indirect techniques (bioluminescence, impedimetry, and the like) have been proposed. However, they require specific equipment, are more or less suitable for heterogeneous cultures such as milk and milk products, and in practice are hardly used in the dairy industry.

It has also been proposed to directly assay these proteases; these assays are carried out either on the basis of the enzymatic activity, or directly by immunochemical quantification of the proteases.

Assay of the enzymatic activity is carried out for example by determining hydrolysis of natural or artificial substrates, releasing labelled products (coloured, fluorescent or radioactive). By way of example, the HPA technique [CLIFFE and LAW, J. Dairy Sci., 49, 209–219 (1982)] may be mentioned in which the substrate is collagen denatured by covalent bonding with a blue dye. This technique makes it possible to detect proteases produced by about $2 \times 10^6$ psychrotrophs/ml.

Immunochemical methods have been proposed, for example, for proteinase P1 from *Pseudomonas fluorescens* [BRIKELAND et al., Appl. Environ. Microbiol., 49, 382–387]. Assay of this proteinase by the ELISA technique makes it possible to detect the equivalent of about $10^7$ psychrotrophs/ml.

Other techniques involve the measurement of amino acids or non-protein nitrogen which are released by proteolysis. These methods are however difficult to implement since they require prior separation of the hydrolysis products. They make it possible to detect about $5 \times 10^6$ psychrotrophs/ml.

Finally, other methods are based on the detection of products of casein hydrolysis. For K-casein, it has been proposed to assay the two degradation products which are K-paracasein and caseinomacropeptide (CMP).

At present, K-paracasein is only detectable by electrophoresis, which represents a relatively toilsome method.

In the case of CMP, which is a glycopeptide, it has been proposed to assay it by measuring sialic acid, N-acetylneuraminic acid or by chromatography on DEAE cellulose. However, these are toilsome techniques and the results obtained are not very precise.

In order to have a method combining speed, ease of use and reliability, the inventors embarked upon the development of an immunological technique for the assay of CMP.

They therefore sought to obtain anti-CMP antibodies (COLLIN et al. Communication at the XXth International Dairy Congress, Montreal, 8–12 Oct. 1990].

However, the preparation of CMP by hydrolysis of K-casein requires purification procedures, which are also long and costly, for removing any contamination by non-hydrolysed K-casein. In addition, the inventors observed that even when a perfectly purified CMP preparation, uncontaminated by K-casein, is used as immunogen, antibodies exhibiting cross-reactivity with non-hydrolysed K-casein are nevertheless obtained; these reactions are not eliminated even after several affinity chromatographies.

The objective of the present invention is the production of antigenic molecules which are easy to prepare by chemical synthesis, which carry the antigenic determinants of CMP, and which can be used for induction of anti-CMP antibodies.

The inventors observed that, although CMP is a glycopeptide, some non-glycosylated peptides, representing fragments of the CMP sequence, had the desired properties.

The subject of the present invention is an antigenic peptide whose amino acid sequence comprises a fragment of the CMP sequence, which peptide is characterised in that it carries at least one epitope of CMP, and in that it is chosen from the group consisting of the peptides comprising the following sequence Met-Ala-Ile-Pro-Pro, designated in the list of sequences in the appendix under the number SEQ. ID No. 1; (amino acids 106 to 110 of K-casein of cow's milk)

and the peptides comprising at least 5 consecutive amino acids of one of the following sequences Ser-Pro-Pro-Glu-Ile-Asn-Thr-Val-Gln-Val; Lys-Thr-Glu-Ile-Pro-Thr-Ile-Asn-Thr-Ile; Thr-Ile-Ala-Ser-Gly-Glu-Pro-Thr-Ser-Thr; Asp-Ser-Pro-Glu-Val-Ile-Glu-Ser-Pro-Pro; respectively designated in the list of sequences in the appendix under the numbers SEQ. ID No. 2, (amino acids 155 to 164 of cow's milk) SEQ. ID No. 3, (amino acids 116 to 125 of cow's milk) SEQ. ID No. 4 (amino acids 124 to 133 of cow's milk) and SEQ. ID No. 5. (amino acids 148 to 157 of cow's milk).

According to a preferred embodiment of the present invention, the said peptide comprises at least 8 consecutive amino acids of one of the sequences SEQ. ID No. 2, SEQ. ID No. 3, SEQ. ID No. 4 and SEQ. ID No. 5.

In addition, the inventors observed that among the peptides obtained, some exhibited no or little cross-reactivity with K-casein. When these peptides are used as immunogens, they make it possible to obtain specific anti-CMP antibodies.

"Specific anti-CMP antibodies" are understood to mean antibodies which recognise CMP and which do not exhibit cross-reactivity, or alternatively, only reactions which are easy to eliminate by affinity chromatography, with K-casein. The production of such antibodies using fragments of CMP is surprising given that it was previously found to be impossible to eliminate cross-reactions with K-casein when CMP is used as immunogen.

According to another preferred embodiment of the present invention, the said peptide is chosen from the group consisting of the peptides essentially consisting of the following sequence SEQ. ID No. 6 (amino acids 106 to 116 of cow's milk) Met-Ala-Ile-Pro-Pro-Lys-Lys-Asn-Gln-Asp-Lys, the peptides essentially consisting of one of the following sequences Met-Ala-Ile-Pro-Pro-Lys (SEQ. ID NO:7); Met-Ala-Ile-Pro-Pro-Lys-Lys (SEQ. ID NO:8); Met-Ala-Ile-Pro-Pro-Lys-Lys-Asn (SEQ. ID NO:9); Met-Ala-Ile-Pro-Pro-Lys-Lys-Asn-Gln (SEQ. ID NO:10); Met-Ala-Ile-Pro-Pro-Lys-Lys-Asn-Gln-Asp (SEQ. ID NO:11).

According to yet another preferred embodiment of the present invention, the said peptide additionally comprises a cysteine at its C-terminal end.

Figure 1A:
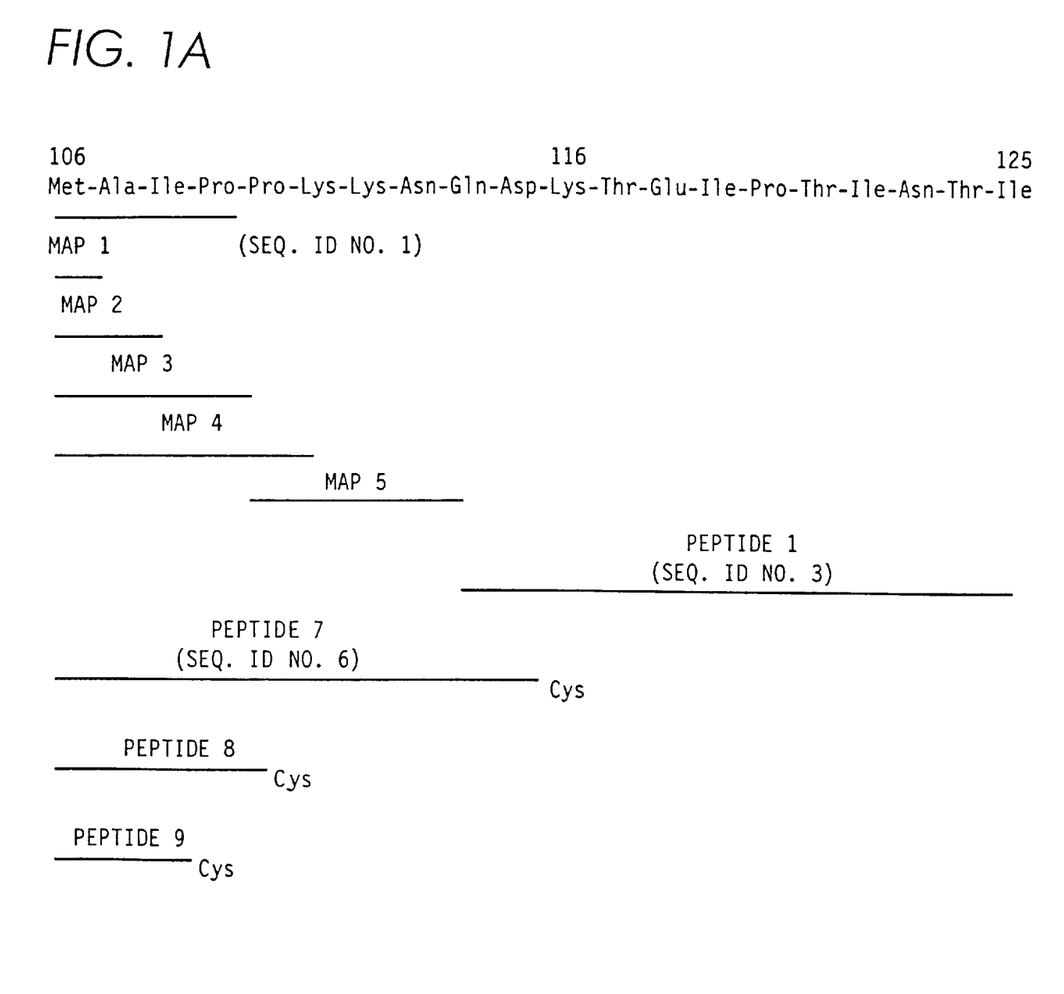
FIG. 1 graphically represented synthetic peptides (SEQ. ID NOS:1–6) which constitute fragments of the sequence of cow's milk CMP.
Figure 1B:
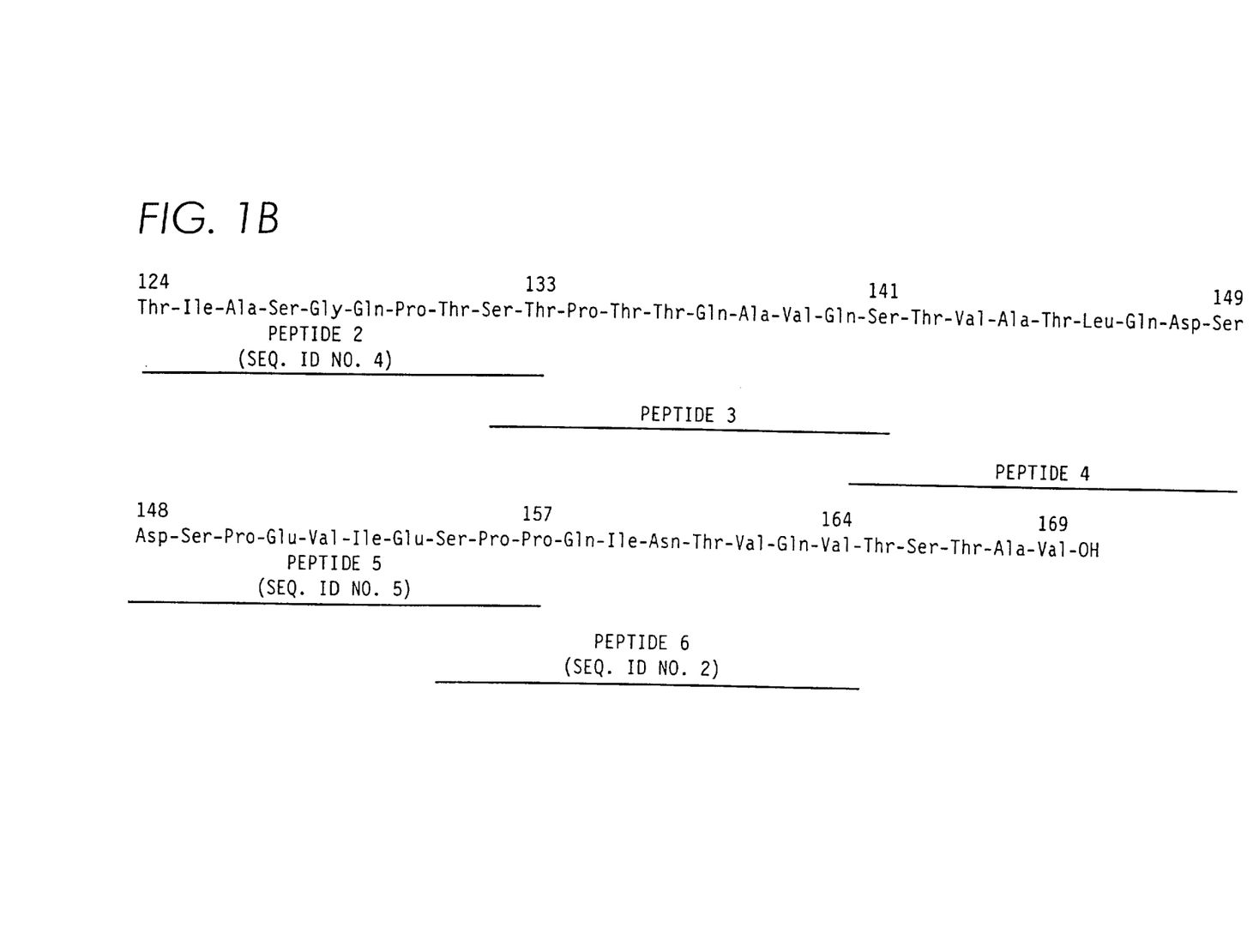

The position of the peptides of the sequences SEQ. ID Nos. 1, 2, 3, 4, 5 and 6, relative to the sequence of CMP, is indicated in FIG. 1, as well as that of the peptides used for the construction of MAP.

The invention also encompasses antigenic compositions, which compositions are characterised in that they essentially comprise, as constituent, at least one peptide as defined above.

Antigenic compositions conforming to the invention include in particular, not only the above-defined peptides, but also the more complex antigens obtained by coupling the said peptides to carrier proteins, as well as the MAPs (multiple antigenic peptides) [TAM, Proc. Natl. Acad. Sci. U.S.A., 85, 5409–5413, (1988)] obtained from the said peptides.

These compositions can in particular be used both as immunogens for induction of anti-CMP antibodies, and as reagents for the detection and assay of CMP.

Compositions comprising peptides containing the sequence SEQ. ID No. 1 (for example the compositions comprising the peptides SEQ. ID No. 6 or fragments thereof) make it possible to obtain specific anti-CMP antibodies.

Compositions comprising the peptide of sequence SEQ. ID No. 2 or fragments thereof, make it possible to obtain species-specific antibodies recognising only cow's milk CMP, which makes it possible to detect the presence of cow's milk in milk or other milk products supposedly obtained from other species, in particular in sheep's milk, in goat's milk and even in milk from bovines such as buffaloes.

The subject of the present invention is also a process for preparing anti-CMP antibodies, which process is characterised in that it comprises a stage in which an animal is immunised with an antigenic composition as defined above.

The invention also includes the anti-CMP antibodies obtained using as immunogen, a composition conforming to the invention.

According to a preferred embodiment of the present invention, the said antibodies are monoclonal antibodies.

According to another preferred embodiment of the present invention, the said antibodies are polyclonal antibodies.

The subject of the present invention is additionally a process for evaluating proteolysis of milk and milk products, the said process is characterised in that it comprises a stage in which a specific anti-CMP antibody conforming to the invention, which is produced against a peptide comprising the sequence SEQ. ID No. 1, is placed in contact with a milk or milk product sample to be tested, and a stage where the detection and/or assay, by any appropriate means, of the antigen/antibody complex formed during the preceding stage is carried out.

According to a preferred embodiment of the process conforming to the invention, the specific anti-CMP antibody used is produced against a peptide of sequence SEQ. ID No. 6 or one of its fragments.

Anti-CMP antibodies which recognise both K-casein and CMP may be used as control to evaluate the total quantity of K-casein (hydrolysed or non-hydrolysed) present.

The process conforming to the invention thus made it possible for the inventors to detect the existence of K-casein proteolysis in yogurts, the degree of which proteolysis varies according to the strains used for manufacturing the yogurt. This process can therefore be advantageously applied for the selection of strains according to their capacity to produce CMP by K-casein hydrolysis.

The subject of the present invention is additionally a process for detecting the presence of cow's milk CMP in milk and milk products, which process is characterised in that it comprises a stage in which an antibody produced against a peptide of sequence SEQ. ID No. 2 or a fragment of the said peptide is placed in contact with a milk or a milk product sample to be tested, and a stage where the detection and/or assay, by any appropriate means, of the antigen/antibody complex formed during the preceding stage is carried out.

The means for detecting and assaying an antigen/antibody complex are well known to a person skilled in the art; the various methods ELISA, RIA and the like may be mentioned by way of non-limiting example among the procedures most commonly used.

The subject of the present invention is also diagnostic reagents for the assay of CMP, which reagents are characterised in that they comprise at least one peptide or one antigenic composition or alternatively at least one anti-CMP antibody conforming to the invention. The said antibody or the said peptide are optionally coupled to an appropriate marker (chemical, enzymatic or radioactive) which allows the reaction product to be visualised.

The present invention will be more clearly understood with the aid of the additional description below, which refers to examples for using an antigenic composition conforming to the invention for the production of anti-CMP antibodies and to the use of the said antibodies for the evaluation of milk proteolysis.

Naturally, however, these examples are given solely by way of illustration of the subject of the invention and do not constitute in any way a limitation thereof.

I.—PRODUCTION OF ANTI-CMP ANTIBODIES

The peptides are synthesised by the method of MERRIFIELD, using the procedure described in the fascicule "Synthetic polypeptides as antigens", [VAN REGENMORTEL, BRIAND, MULLER, PLANE, Ed. Elsevier (1988)], and then purified by chromatography. After purification, the peptide is coupled to a carrier protein either ovalbumin on the amino acid cysteine using the coupling agent MBS (M-maleimidobenzoyl-N-hydroxysuccinimide ester), or bovine serum albumin on the amino acid tyrosine using the coupling agent BDB (bisdiazobenzidine).

EXAMPLE 1

Preparation of a polyclonal serum

Rabbits are immunised against the synthetic peptide, according to the following procedure for the first injection, 200 µg of the peptide are dissolved in 1 ml of a mixture, in equal volumes, of physiological saline and complete Freund's adjuvant. Booster injections are performed every 3 weeks with 200 µg of peptide in emulsion in incomplete Freund's adjuvant.

Blood samples are collected from 10 days onwards after the 1st injection, and the serum is recovered.

In order to eliminate cross-reactions with K-casein, the serum is adsorbed onto a K-casein gel consisting of 10 mg of K-casein supplemented with 200 mg of bovine serum albumin and a coupling agent, 2.5% glutaraldehyde. The polymerised gel is preserved in a 0.1M phosphate buffer, pH 7.2, at 4° C. In a first instance, the gel is centrifuged for 15 min at 18600 g, at 4° C. It is then centrifuged for 15 min at 23600 g, at 4° C. in order to remove the phosphate buffer.

The anti-CMP serum is added onto the gel, in an amount of 310 mg of freeze-dried serum in 1 ml of phosphate buffer. This mixture is stirred for 2 h, at room temperature, and then overnight at 4° C. Then the gel is centrifuged for 15 min at 23600 g, at 4° C. The supernatant is recovered and the gel is rinsed with 0.25 ml of phosphate buffer. It is then recentrifuged for 15 min at 23600 g in order to recover all the entrapped serum. The supernatant thus obtained is added to the first supernatant.

EXAMPLE 2

Production of anti-CMP monoclonal antibodies

Balb/c BYJICO mice are immunised by a first intraperitoneal injection of 100 µg of ovalbumin-coupled peptide, emulsified in complete Freund's adjuvant. On the 17th day, an intraperitoneal injection of 50 µg of ovalbumin-coupled peptide is carried out in the presence of incomplete Freund's adjuvant, and an intravenous injection of 10 µg of ovalbumin-coupled peptide is carried out without adjuvant. On the 20th day, the mice are sacrificed, the spleen is removed and the splenocytes are fused with myelomatous cells according to the method of MILSTEIN and KOHLER [Nature, 256, 495–497 (1975)]. Screening of the hybrids obtained is carried out on the peptide which served for the immunisation coupled to bovine serum albumin.

EXAMPLE 3

Comparison of the antigenic properties of various peptides from CMP

Synthetic peptides which constitute fragments of the sequence of cow's milk CMP, represented in FIG. 1, under the numbers 1 to 9 (peptide 7 corresponds to the peptide SEQ. ID No. 6 and peptide 8 to the first 6 amino acids of the said sequence; a Cys residue was added at the C-terminal end of these two peptides) were used to prepare antibodies according to the process described in Example 1.

The assay was carried out by ELISA according to the following procedure, 100 µl of a solution of CMP at 2 µg/ml or 100 µl of a solution of K-casein at 6 µg/ml are placed in the wells of microtitre plates. Adsorption of these antigens is carried out by incubating the plates overnight at 4° C. The wells are then washed three times with 350 µl of PBS-Tween and are saturated with 250 µl of PBS-Tween+1% gelatine. The plate is incubated for 1 h at 37° C. 100 µl of the antibody (1/1000 dilution) produced against one of the peptides 1 to 8 are placed in the wells of each of the plates which are then incubated for 1 hour 30 min at 37° C.

After 3 washes with 350 µl of PBS-Tween, there are added 100 µl, per well, of a peroxidase-coupled antirabbit IgG antibody and diluted 1/2000 in PBS-Tween, and the plate is incubated for 45 min at 37° C. After 3 new washes with PBS-Tween, the reaction is visualised. The substrate used is 3,3',5,5'-tetramethylbenzidine (TMB), diluted 1/10 in 0.1M citrate buffer, pH 5+$H_2O_2$. 75 µl are placed in each well and the plate is incubated for 15 min at 37° C.

The reaction between the peroxidase and the TMB produces a blue colour. This reaction is stopped by the addition of 25 µl of 1N hydrochloric acid per well. The substrate then becomes yellow in colour. The results are evaluated by measuring the OD at 450 nm.

The results are represented in Table I below, (+) indicates a positive reaction, (−) indicates a negative reaction, the number of + signs indicates the intensity of the coloration observed

TABLE I

| | ANTIGEN | |
|---|---|---|
| ANTIBODY | CMP | K-casein |
| 1 | +++ | +++ |
| 2 | ++ | ++ |
| 3 | − | − |
| 4 | − | − |
| 5 | +++ | +++ |
| 6 | +++ | +++ |
| 7 | +++ | + |
| 8 | +++ | − |
| 9 | − | − |

II.—USE OF ANTI-CMP ANTIBODIES FOR ASSAYING CMP IN MILK AND MILK PRODUCTS

The assay is carried out on a solution of the test sample which has been previously treated by ultra-filtration so as to remove the maximum amount of milk proteins which, by adsorbing onto the wells, would interfere with the adsorption of CMP. This assay is carried out by the ELISA method as described in Example 3 above.

A known amount of purified antigen (for example 100 µl of a solution of CMP at 2 µg/ml; the peptides or MAPs conforming to the invention may also be used to replace the CMP) is adsorbed onto the plate.

If it is desired to carry out the assay on a non-ultrafiltered sample, it is preferable to carry out a competitive type ELISA assay.

After washing and saturation of the plate, the antigen-antibody reaction is carried out in the presence of successive dilutions of the antigenic solution to be assayed.

The reaction product is visualised as indicated in Example 3 above.

The amount of CMP present in the sample to be assayed is evaluated by comparison with a calibration series obtained from known dilutions of CMP.

EXAMPLE 4

Assay of CMP in milk

The antibodies used for this assay were produced against the peptide 7 (SEQ. ID No. 6+Cys).

A study on 110 milk samples, from 4 cheese factories, showed that 13% of these samples containing on average $2 \times 10^5$ germs per milliliter on their arrival in the laboratory, contained more than 5 µg of CMP per milliliter. After preserving for two days at +4° C., the average number of germs increased to $4 \times 10^6$ germs/ml and 26% of the samples contained more than 5 µg of CMP per milliliter.

In addition, 9 UHT milk samples were examined before and after centrifugation and their destabilisation was evaluated. The samples which remained stable after centrifugation were heated between 60° and 100° C. and their destabilisation temperature was noted.

It is observed that highly destabilised milks have a high CMP concentration (>80 µg/ml) while stable milks contain 10 µg of CMP per ml, or even less. A milk which remains stable after centrifugation, but which is destabilised during heating, contains 43.4 µg of CMP per ml. The results reveal a relationship between proteolysis of K-casein, evaluated by assaying CMP, and destabilisation of UHT milks.

EXAMPLE 5

Use of antibodies conforming to the invention for the assay of CMP in cheese and demonstration of the species-specificity of antibodies directed against the peptide SEQ ID No. 2

A rabbit polyclonal antibody directed against the peptide SEQ ID No. 2 and prepared according to the procedure described in Example 1 is used.

An aqueous extraction in 10 ml of 0.05M phosphate buffer pH 7.2 is carried out on 5 g of cheese by mixing using a beater. The presence or the absence of cow's CMP is determined on the aqueous phase obtained by centrifuging the solution obtained after mixing, using the inhibition ELISA method described above.

Figure 2:
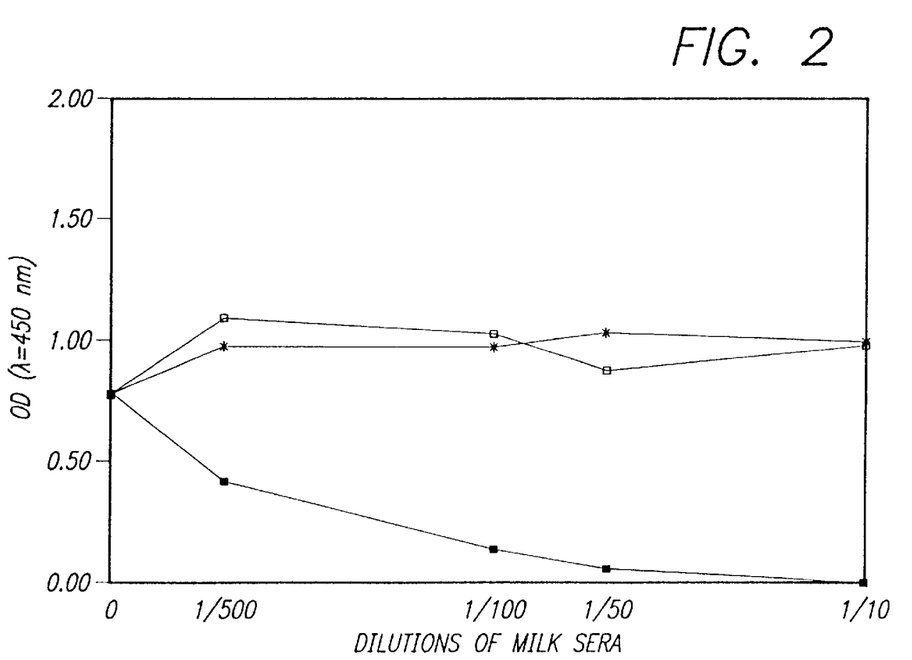
FIG. 2 graphically presents the results of an assay of CMP in cheese using the antibodies of the present invention.

The results are illustrated by FIG. 2. On the x-axis are indicated the dilutions of the aqueous extracts (■) cow; (□) sheep; (*) goat; on the y-axis, the OD 450.

---

---

We claim:

1. An antigenic peptide chosen from the group consisting of peptides having any of the following sequences:
   Met-Ala-Ile-Pro-Pro-Lys (SEQ. ID NO.: 7);
   Met-Ala-Ile-Pro-Pro-Lys-Lys (SEQ. ID NO.: 8);
   Met-Ala-Ile-Pro-Pro-Lys-Lys-Asn (SEQ. ID NO.: 9);
   Met-Ala-Ile-Pro-Pro-Lys-Lys-Asn-Gln (SEQ. ID NO.: 10);
   Met-Ala-Ile-Pro-Pro-Lys-Lys-Asn-Gln-Asp (SEQ. ID NO.: 11);
   Met-Ala-Ile-Pro-Pro-Lys-Lys-Asn-Gln-Asp-Lys (SEQ. ID No. 6); and
   comprising a cysteine linked at its C-terminal end through a peptide linkage.

2. An antigenic composition for inducing anti-caseinomacropeptide antibodies, said composition comprising an effective immunizing amount of:
   a) at least one peptide chosen from the group consisting of the peptides according to claim 1;
   at least one product of the coupling of a peptide having any of the sequences of SEQ ID NO:6, SEQ ID NO:7, SEQ ID NO:8, SEQ ID NO:9, SEQ ID NO:10, and SEQ ID NO:11, with a carrier protein; or of
   c) at least one multiple antigenic peptide (MAP) derived from a peptide having the sequence of SEQ ID No7; and a pharmaceutically acceptable carrier.

3. A process for preparing anti-caseinomacropeptide antibodies, said process comprising the steps of:
   immunizing an animal with an antigenic composition according to claim 2; and
   collecting anti-caseinomacropeptide antibodies produced by the immunized animal.

4. Anti-caseinomacropeptide antibodies obtained by a process comprising the steps of:
   immunizing an animal with an antigenic composition according to claim 2; and
   collecting anti-caseinomacropeptide antibodies produced by the immunized animal, wherein the antibodies bind to an epitope having the sequence of SEQ ID NO.: 7.

5. The anti-caseinomacropeptide antibodies of claim 4, wherein said antibodies are monoclonal antibodies.

6. The anti-caseinomacropeptide antibodies of claim 4, wherein said antibodies are polyclonal antibodies.

7. A process for evaluating proteolysis of milk and milk products, said process comprising a step in which the anti-caseinomacropeptide antibodies of claim 4, are contacted with the milk or milk product sample to be tested, in conditions allowing the formation of an antigen/antibody complex between said antibody and the epitope having the sequence SEQ ID NO.: 7 borne by said caseinomacropeptide, and a step of detecting said antigen/antibody complex, if present as compared to a calibration sample.

8. A reagent for the detection and assay of caseinomacropeptide, which reagent comprises at least an antigenic composition according to claim 2.

9. A reagent for the detection and assay of caseinomacropeptide, which reagent comprises at least one anti-caseinomacropeptide antibody according to claim 4.

10. An antigenic peptide consisting of a fragment of the caseinomacropeptide sequence having the following sequence:

Ser-Pro-Pro-Glu-Ile-Asn-Thr-Val-Gln-Val (SEQ ID NO:2)

and comprising a cysteine linked at its C-terminal end through a peptide linkage.

11. An antigenic composition for inducing anti-caseinomacropeptide antibodies, said composition comprising an effective immunizing amount of:

a) at least one peptide according to claim 10;

b) at least one product of the coupling of a peptide having the sequence SEQ ID NO:2, with a carrier protein; or c) at least one multiple antigenic peptide (MAP) derived from a peptide having the sequence SEQ ID NO:2;

and a pharmaceutically acceptable carrier.

12. A process for preparing anti-caseinomacropeptide antibodies, said process comprising the steps of:

immunizing an animal with an antigenic composition according to claim 11; and collecting anti-caseinomacropeptide antibodies produced by the immunized animal.

13. The anti-caseinomacropeptide antibodies obtained by the process of claim 12.

14. The anti-caseinomacropeptide antibodies according to claim 13, which are monoclonal antibodies.

15. The anti-caseinomacropeptide antibodies according to claim 13, which are polyclonal antibodies.

16. A reagent for the detection and assay of cow's milk caseinomacropeptide or of caseinomacropeptide domain of cow's milk K-casein, which reagent comprises at least an antigenic composition according to claim 11.

17. A reagent for the detection and assay of cow's milk caseinomacropeptide or of caseinomacropeptide domain of cow's milk K-casein, which reagent comprises at least one anti-caseinomacropeptide antibody according to claim 13.

18. A process for detecting the presence of cow's milk caseinomacropeptide or cow's milk K-casein in milk and milk products, said process comprising a step in which an anti-caseinomacropeptide antibody of claim 13, is contacted with the milk or milk product sample to be tested, in conditions allowing the formation of a specific antigen/antibody complex between said antibody and cow's milk caseinomacropeptide or caseinomacropeptide domain of cow's milk K-casein, and a step of detecting said antigen/antibody complex, if present.

* * * * *

UNITED STATES PATENT AND TRADEMARK OFFICE
CERTIFICATE OF CORRECTION

PATENT NO. : 5,846,732
DATED : December 8, 1998
INVENTOR(S) : Jean-Claude Collin
                 Jean-Louis Perrod It is certified that error appears in the above-identified patent and that said Letters Patent is hereby corrected as shown below:

On the title page, add item [73] Assignee, Systems Bio-Industries, France--.

Signed and Sealed this

Tenth Day of August, 1999

Attest:

Q. TODD DICKINSON

*Attesting Officer*      Acting Commissioner of Patents and Trademarks